United States Patent [19]

Baumann et al.

[11] 4,260,604
[45] Apr. 7, 1981

[54] PYRIDAZINONYL-(DI)(THIO)-PHOSPHORIC (PHOSPHONIC) ACID ESTERS AS PESTICIDES

[75] Inventors: Annegrit Baumann, Mannheim; Heinrich Adolphi, Limburgerhof, both of Fed. Rep. of Germany; Rolf Huber, Boonton, N.J.; Karl Kiehs, Lampertheim, Fed. Rep. of Germany

[73] Assignee: BASF Aktiengesellschaft, Fed. Rep. of Germany

[21] Appl. No.: 82,161

[22] Filed: Oct. 5, 1979

Related U.S. Application Data

[63] Continuation of Ser. No. 949,738, Oct. 19, 1978, abandoned.

[30] Foreign Application Priority Data

Oct. 14, 1977 [DE] Fed. Rep. of Germany ....... 2746207

[51] Int. Cl.$^3$ .................. C07F 9/65; A01N 57/24; A01N 57/32; A01N 57/16
[52] U.S. Cl. .................................. 424/200; 544/232
[58] Field of Search .......................... 544/232; 424/200

[56] References Cited

U.S. PATENT DOCUMENTS

| | | |
|---|---|---|
| 2,739,937 | 8/1956 | Du Breuil ............................ 544/232 |
| 2,758,115 | 8/1956 | Lorenz ................................ 260/248 |
| 3,310,560 | 3/1967 | Schonbeck .......................... 544/232 |
| 4,013,657 | 3/1977 | Hofer et al. ........................ 544/232 |
| 4,058,603 | 11/1977 | Hofer et al. ........................ 544/232 |
| 4,097,592 | 6/1978 | Hofer et al. ........................ 544/232 |

FOREIGN PATENT DOCUMENTS

1496626 12/1977 United Kingdom ..................... 544/232
1512529 6/1978 United Kingdom ..................... 544/232

OTHER PUBLICATIONS

Feuer et al., Chem. Abs. 54, 4603f, (1959).

*Primary Examiner*—Mark L. Berch
*Attorney, Agent, or Firm*—Keil & Witherspoon

[57] ABSTRACT

New pyridazinonyl-(di)(thio)-phosphoric (phosphonic) acid esters of the formula

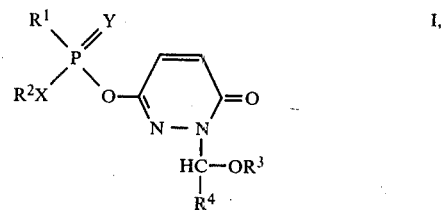

where X and Y each denote oxygen or sulfur, $R^1$ denotes linear or branched alkyl of 1 to 4 carbon atoms, alkoxy of 1 to 4 carbon atoms, mono- or dialkylamino of 1 to 4 carbon atoms in each alkyl, phenyl, or benzyl, $R^2$ denotes linear or branched alkyl of 1 to 4 carbon atoms, phenyl or benzyl, $R^3$ denotes linear or branched alkyl of 1 to 4 carbon atoms or phenyl, $R^4$ denotes linear or branched alkyl of 1 to 4 carbon atoms, or $R^3$ and $R^4$, together with the oxygen and the carbon atom whose substituents they are, form a 5- or 6 membered saturated ring which may be substituted by alkyl of 1 to 4 carbon atoms, which are effective against pests, especially insects and Arachnida, pesticides containing these pyridazinonyl-(di)(thio)-phosphoric (phosphonic) acid esters as active ingredients, and a process for combating pests with these active ingredients.

The present invention relates to new pyridazinonyl-(di)(thio)-phosphoric (phosphonic) acid esters, a process for their manufacture, and pesticides, especially insecticides and acaricides, containing these compounds as active ingredients.

8 Claims, No Drawings

PYRIDAZINONYL-(DI)(THIO)-PHOSPHORIC (PHOSPHONIC) ACID ESTERS AS PESTICIDES

This is a continuation of application Ser. No. 949,738 filed Oct. 19, 1978, now abandoned.

The pyridazinonyl-(di)(thio)-phosphoric (phosphonic) acid esters according to invention of the formula

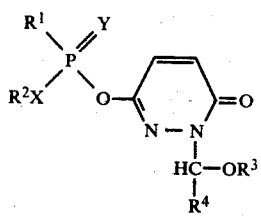

where X and Y each denote oxygen or sulfur, $R^1$ denotes linear or branched alkyl of 1 to 4 carbon atoms, alkoxy of 1 to 4 carbon atoms, mono- or dialkylamino of 1 to 4 carbon atoms in each alkyl, phenyl, or benzyl, $R^2$ denotes linear or branched alkyl of 1 to 4 carbon atoms, phenyl or benzyl, $R^3$ denotes linear or branched alkyl of 1 to 4 carbon atoms or phenyl, $R^4$ denotes linear or branched alkyl of 1 to 4 carbon atoms, or $R^3$ and $R^4$, together with the oxygen and the carbon atom whose substituents they are, form a 5- or 6-membered saturated ring which may be substituted by alkyl of 1 to 4 carbon atoms, are eminently suitable for combating injurious and troublesome articulata from the class of insects and Arachnida.

In formula I, $R^1$ preferably denotes linear or branched alkyl or alkoxy of 1 to 3 carbon atoms, or phenyl, $R^2$ and $R^3$ preferably denote linear or branched alkyl of 1 to 4 carbon atoms, or phenyl, and $R^4$ preferably denotes linear or branched alkyl of 1 to 3 carbon atoms; $R^3$ and $R^4$ also form, together with the atoms whose substituents they are, preferably tetrahydrofuran or tetrahydropyran rings which may be substituted by alkyl of 1 to 4 carbon atoms, preferably methyl.

Preferred compounds of the formula I are those in which X and Y denote oxygen or sulfur, $R^1$ denotes ethoxy, $R^2$ denotes ethyl or n-propyl, $R^3$ denotes linear or branched alkyl of 1 to 4 carbon atoms and $R^4$ denotes linear or branched alkyl of 1 to 3 carbon atoms, or $R^3$ and $R^4$, together with the oxygen and the carbon atom whose substituents they are, form a tetrahydrofuran or tetrahydropyran ring.

The new pyridazinoyl-(di)(thio)-phosphoric (phosphonic) acid esters of the formula I are obtained by reaction of pyridazinonyl-(di)(thio)-phosphoric (phosphonic) acid esters of the formula

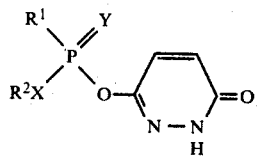

where $R^1$, $R^2$, X and Y have the above meanings, with enol ethers of the formula

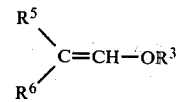

where $R^3$ has the above meanings, $R^5$ denotes hydrogen or methyl, $R^6$ denotes hydrogen or alkyl of 1 to 3 carbon atoms, and $R^3$ and $R^5$ together denote a methylene chain of 2 or 3 carbon atoms which may be substituted by alkyl of 1 to 4 carbon atoms, in the presence of a catalytic amount of acid and an inert solvent or diluent.

Examples of suitable catalytically active acids are inorganic or organic acids and Lewis acids, e.g., HCl, HBr, HF, $H_2SO_4$, $H_3PO_4$, $HClO_4$, $Cl_3CCOOH$,

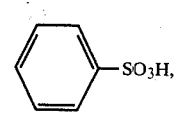

$SOCl_2$, $BF_3C(C_2H_5)_2$, and $ZnCl_2$.

Examples of suitable solvents or diluents are aromatic hydrocarbons, such as benzene, toluene, xylenes, chlorobenzene and nitrobenzene; chlorinated or nitrated aliphatic hydrocarbons, such as dichloromethane, chloroform, carbon tetrachloride, 1,2-dichloroethane and nitromethane; aliphatic nitriles, such as acetonitrile and propionitrile; acyclic and cyclic ethers, such as diethyl ether, diisopropyl ether, diglycol dimethyl ether, tetrahydrofuran and dioxane; and acyclic and cyclic ketones, such as acetone, methyl ethyl ketone, diethyl ketone, methyl propyl ketone and cyclohexanone.

The reaction temperature may be varied within a wide range; generally, the reaction is carried out at from 0° to 100° C., preferably from 30° to 50° C., unless the boiling point of the solvent sets the upper limit.

The pyridazinonyl-(di)(thio)-phosphoric (phosphonic) acid esters of the formula II used as starting materials may be obtained by the conventional reaction of 3-hydroxypyridazinone-(6) with the appropriately substituted thiono-(thiolo)-phosphoric (phosphonic) acid ester chlorides of the formula

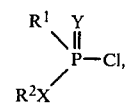

where $R^1$, $R^2$, X and Y have the above meanings (J. Org. Chem., 26, 3382–3386, 1961).

The preparation of the enol ethers of the formula III is also known (Houben-Weyl, Methoden der organischen Chemie, 6/3, 90 et seq., Georg Thieme-Verlag, Stuttgart, 1965).

To carry out the process, a slight excess (advantageously, a 10% excess) of enol ether of the formula III over starting material of the formula II is used. A larger excess offers no advantages. Generally, the pyridazinonyl derivative is placed in a vessel together with the solvent or diluent, a few drops of acid are added, followed by the enol ether. After a reaction period of from 1 to several hours at elevated temperature, the batch is cooled to room temperature, made weakly alkaline, e.g., with an amine, and worked up by conventional methods, e.g., washing, drying and distillation.

The new compounds are obtained in the form of yellow oils. They are characterized by their refractive index and elemental analysis.

The following examples demonstrate the preparation of the compounds according to the invention.

EXAMPLE 1

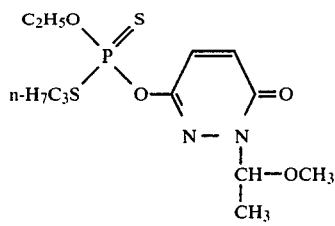

2 drops of thionyl chloride in 0.1 mole of O-ethyl-S-n-propyl-O-3-pyridazinon-(5)-yl-dithiophosphoric acid ester are placed in a vessel containing toluene. At from 0° to 5° C., 0.11 mole of methyl vinyl ether is then added all at once. The mixture is stirred for one hour at from 0° to 5° C., after which the temperature is slowly raised, while stirring continuously, over a period of 4 hours to 50° C.

After the mixture has been cooled to room temperature, it is made slightly alkaline with triethylamine and extracted 3 times with water; the toluene phase is dried over sodium sulfate and concentrated.

The product obtained is taken up in petroleum ether, and unreacted starting material is filtered off. After the petroleum ether solution has been concentrated, the end product is obtained as an oil which analyzes as pure; yield: 85% of theory.

$n_D^{25}$: 1.5416 calc.: C 40.9 H 6.0 N 7.9 S 18.2 P 8.8 O 18.2. found: C 40.2 H 5.8 N 8.1 S 18.9 P 9.2.

EXAMPLE 2

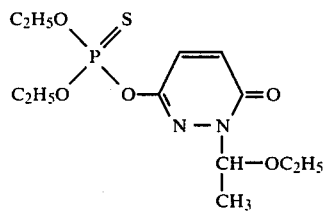

The compound is prepared analogously to Example 1. The solvent is acetonitrile; the vinyl ether is added at room temperature. The end product is obtained as an oil which analyzes as pure; yield: 79% of theory.

$n_D^{25}$: 1.4990 calc.: C 42.9 H 6.25 N 8.3 S 9.5 P 9.2. found: C 42.8 H 6.30 N 8.3 S 9.5 P 9.2.

EXAMPLE 3

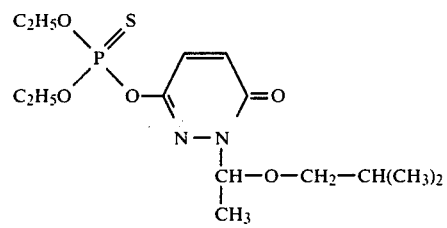

The reaction is carried out at room temperature, as in Example 1, in tetrahydrofuran. One drop of $H_3PO_4$ is added as catalyst. The end product is obtained as an oil; yield 82% of theory.

$n_D^{25}$: 1.4915 calc.: C 45.7 H 6.9 N 7.1 S 16.3 P 7.9 O 16.2. found: C 44.9 H 6.6 N 7.4 S 16.4 P 8.4.

The following compounds of the formula

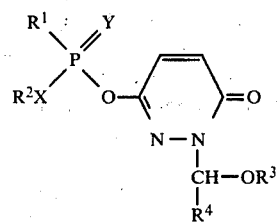

were synthesized in the same way:

| No. | R$^1$ | R$^2$ | X | Y | R$^3$ | R$^4$ | $n_D^{25}$ |
|---|---|---|---|---|---|---|---|
| 4 | C$_2$H$_5$O | C$_2$H$_5$ | O | S | | | 1.5248 |
| 5 | C$_2$H$_5$O | C$_2$H$_5$ | O | S | CH$_3$ | CH$_3$ | 1.5083 |
| 6 | C$_2$H$_5$O | n-C$_3$H$_7$ | S | S | i-C$_4$H$_9$ | CH$_3$ | 1.5261 |
| 7 | C$_2$H$_5$O | n-C$_3$H$_7$ | S | S | | | 1.5570 |
| 8 | C$_2$H$_5$O | C$_2$H$_5$ | O | S | C$_2$H$_5$ | i-C$_3$H$_7$ | 1.4978 |
| 9 | C$_2$H$_5$O | C$_2$H$_5$ | O | S | | | 1.5281 |
| 10 | C$_2$H$_5$O | C$_2$H$_5$ | O | S | CH$_3$ | n-C$_3$H$_7$ | m.p. = 47–49° C. |
| 11 | C$_2$H$_5$O | n-C$_3$H$_7$ | S | S | i-C$_3$H$_7$ | CH$_3$ | 1.5249 |
| 12 | C$_2$H$_5$O | n-C$_3$H$_7$ | S | S | C$_2$H$_5$ | CH$_3$ | 1.5338 |
| 13 | C$_2$H$_5$O | sec.-C$_4$H$_9$ | S | S | CH$_3$ | CH$_3$ | 1.5296 |
| 14 | C$_2$H$_5$O | sec.-C$_4$H$_9$ | S | S | i-C$_4$H$_9$ | CH$_3$ | 1.5182 |
| 15 | C$_2$H$_5$O | sec.-C$_4$H$_9$ | S | S | | | 1.5494 |

-continued

| No. | R¹ | R² | X | Y | R³ | R⁴ | $n_D^{24}$ |
|---|---|---|---|---|---|---|---|
| 16 | NH—i-C₃H₇ | C₂H₅ | O | S | CH₃ | CH₃ | 1.5140 |
| 17 | NH—i-C₃H₇ | C₂H₅ | O | S | i-C₄H₉ | CH₃ | 1.5045 |
| 18 | NH—i-C₃H₇ | C₂H₅ | O | S |  | | 1.5293 |

| No. | R¹ | R² | X | Y | R³ | R⁴ | $n_D^{24}$ |
|---|---|---|---|---|---|---|---|
| 19 | N(CH₃)₂ | C₂H₅ | O | O | CH₃ | CH₃ | |
| 20 | N(CH₃)₂ | C₂H₅ | O | O | i-C₄H₉ | CH₃ | 1.7065 |
| 21 | N(CH₃)₂ | C₂H₅ | O | O |  | | |
| 22 | C₆H₅ | C₂H₅ | O | S | CH₃ | CH₃ | 1.5585 |
| 23 | C₂H₅O | n-C₃H₇ | S | S | CH₃ | | 1.5450 |
| 24 | C₂H₅O | C₂H₅ | O | S | i-C₃H₇ | CH₃ | 1.4973 |
| 25 | C₂H₅O | C₂H₅ | O | S | CH₃ | i-C₃H₇ | 1.4970 |
| 26 | C₂H₅O | n-C₃H₇ | S | S |  | | 1.5479 |
| 27 | C₂H₅O | n-C₃H₇ | S | S | CH₃ | i-C₃H₇ | 1.5260 |
| 28 | C₂H₅O | sec.-C₂H₉ | S | S | C₂H₅ | CH₃ | 1.5263 |
| 29 | C₂H₅O | sec.-C₄H₉ | S | S | C₂H₅ | i-C₃H₇ | 1.5210 |
| 30 | C₂H₅O | sec.-C₄H₉ | S | S | i-C₃H₇ | CH₃ | 1.5239 |
| 31 | C₂H₅O | sec.-C₄H₉ | S | S | CH₃ | i-C₃H₇ | 1.5212 |
| 32 | C₂H₅ | sec.-C₄H₉ | S | S | CH₃ | | 1.5456 |

| No. | R¹ | R² | X | Y | R₃ | R⁴ | $n_D^{25}$ |
|---|---|---|---|---|---|---|---|
| 33 | C₂H₅O | sec.-C₄H₉ | S | S |  | | 1.5483 |
| 34 | C₂H₅O | sec.-C₄H₉ | S | S | C₂H₅ | C₂H₅ | 1.5207 |
| 35 | C₂H₅O | sec.-C₄H₉ | S | S | C₆H₅ | CH₃ | 1.5620 |
| 36 | C₂H₅O | sec.-C₄H₉ | S | S | CH₃ | n-C₃H₇ | 1.5261 |
| 37 | NH—i-C₃H₇ | C₂H₅ | O | S | C₂H₅ | CH₃ | 1.5131 |
| 38 | NH—i-C₃H₇ | C₂H₅ | O | S |  | | 1.5330 |
| 39 | NH—i-C₃H₇ | C₂H₅ | O | S | C₂H₅ | i-C₃H₇ | 1.5067 |
| 40 | NH—i-C₃H₇ | C₂H₅ | O | S | i-C₃H₇ | CH₃ | 1.5060 |
| 41 | NH—i-C₃H₇ | C₂H₅ | O | S | C₂H₅ | C₂H₅ | 1.5103 |
| 42 | NH—i-C₃H₇ | C₂H₅ | O | S | C₆H₅ | CH₃ | m.p. = 105–106° C. |
| 43 | NH—i-C₃H₇ | C₂H₅ | O | S | CH₃ | n-C₃H₇ | 1.5123 |
| 44 | N(CH₃)₂ | C₂H₅ | O | O | C₂H₅ | CH₃ | 1.4850 |
| 45 | N(CH₃)₂ | C₂H₅ | O | O | C₂H₅ | i-C₃H₇ | 1.4759 |
| 46 | N(CH₃)₂ | C₂H₅ | O | O | i-C₃H₇ | CH₃ | 1.4792 |
| 47 | N(CH₃)₂ | C₂H₅ | O | O | C₂H₅ | C₂H₅ | 1.4752 |

The compounds according to the invention are suitable for effectively combating injurious or troublesome articulata from the class of insects and Arachnida (spiders, mites, ticks).

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarius, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monacha, Pieris brassicae* and *Aporia crataegi;* examples from the Coleoptera order are *Blitophaga undata, Melanotus communis, Linonius californicus, Agriotes lineatus, Agriotes obscurus, Agrilus sinuatus, Meligethes aneneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Psylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar., Ips typographus,* and *Blastophagus piniperda;* examples from the Diptera order are *Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Os-*

*cinella frit, Phorbia coarctata, Phorbia antiqua, Phorbia brassicae,* and *Pogomya hyoscyami;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* an example from the Isoptera order is *Reticulitermes lucifugus.*

Examples of spiders, mites and ticks (Acarina) belonging to the Arachnida class are *Ixodes ricinus, Ornithodorus moubata, Ablyomma americanum, Dermacentor silvarum, Boophilus microplus, Tetranychus telarius, Tetranychus atlanticus, Tetranychus pacificus, Paratetranychus pilosus,* and *Bryobia praetiosa.*

The compounds according to the invention may be successfully employed as pesticides for crop protection, and in the hygiene, stores protection and veterinary sectors.

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethylsulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkal metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose. Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing up to 95% of active ingredient, or even the 100% active ingredient.

Examples of formulations are given below.

I. 500 g of active ingredient from Example 2
 50 g of calcium dodecylbenzene sulfonate
 50 g of ethoxylated oleic acid monoethanolamide
 xylene makeup to 1,000 ml II. 400 g of active ingredient no. 5
 60 g of calcium dodecylbenzene sulfonate
 40 g of ethoxylated oleic acid monoethanolamide
 100 g of N-methylpyrrolidone
 xylene makeup to 1,000 ml III. 3 parts by weight of active ingredient no. 6 is intimately mixed with 97 parts by weight of particulate kaolin. A dust is obtained containing 3% by weight of the active ingredient.

IV. 30 parts by weight of active ingredient no. 10 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

There may be added to the individual active ingredients or mixtures thereof (if desired, immediately before use (tankmix)) oils of various types, herbicides, fungicides, insecticides and bactericides. These agents may be added to the active ingredients according to the invention in a weight ratio of from 1:10 to 10:1.

Examples of active ingredients which may be admixed are as follows:

1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene; C,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethylphosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfynylethyl)-phosphorothioate, O,O-diethyl-S-(2-ethylthioethyl)-phosphorodithioate, O,O-dimethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4triazol-3-yl)-thionophosphate, O,S-dimethyl-phosphoroamidothioate, O,S-dimethyl-N-acetylphosphoramidothioate, γ-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide.

The following examples demonstrate the biological action. The agent used for comparison purposes is O,O-diethyl-S-(4-oxo-1,2,3-benzotriazin-3-[4H]-yl-methyl)-phosphorodithioate (German 927,270). The active ingredients are numbered as in the foregoing table.

EXAMPLE A

Contact action on oriental cockroaches (*Blatta orientalis*)

The bottom of 1-liter preserving jars is treated with acetonic solutions of the active ingredients. After the solvent has evaporated, 5 adult cockroaches are placed in each jar.

The kill rate is determined after 48 hours.

| Active ingredient from Ex. no. | Amount of active ingredient in mg per preserving jar | Kill rate (%) |
| --- | --- | --- |
| 2 | 0.025 | 100 |
| 4 | 0.05 | 100 |
| 5 | 0.025 | 100 |
| 8 | 0.05 | 100 |
|  | 0.02 | 80 |
| 9 | 0.05 | 100 |
| 10 | 0.02 | 100 |
| Comparative agent | 0.1 | 40 |

EXAMPLE B

Breeding experiment with *Drosophila melanogaster*

40 ml of a bran nutrient agar is introduced at 60° C. into plastic bottles (volume: 250 ml); 2 ml of the aqueous active ingredient formulations is then thoroughly mixed in. After having been allowed to cool, the nutrient agar is inoculated with a yeast suspension, and a rolled-up filter paper is placed to lean against the side of the bottle.

From 20 to 40 approximately 6-day old Drosophila are then introduced and the vessels capped.

Assessment takes place after 10 days.

| Active ingredient from Ex. no. | Active ingredient concentration in formulation (mg) |
| --- | --- |
| 1 | 1.0 severe development inhibition |
| 4 | 1.0 severe inhibition |
| 5 | 1.0 severe inhibition |
|  | 0.5 severe inhibition |
| 6 | 1.0 complete inhibition |
| Comparative agent | 2.5 complete inhibition |

| Active ingredient from Ex. no. | Active ingredient concentration in formulation (mg) |
| --- | --- |
| | 1.0 mild inhibition |

EXAMPLE C

Contact action on houseflies (*Musca domestica*)

1 μl of the active ingredient dissolved in acetone is administered by means of a syringe to the ventral abdomen of 4-day old imagoes under slight $CO_2$ narcosis. 20 animals treated in the same way are then placed in a cellophane bag having a volume of approximately 500 ml.

After 4 hours the animals in supine position are counted and the $LD_{50}$ is determined graphically.

| Active ingredient from Ex. no. | $LD_{50}$ (μg/fly) |
| --- | --- |
| 2 | 0.07 |
| 5 | 0.077 |
| 8 | 0.09 |
| 9 | 0.06 |
| Comparative agent | 0.11 |

EXAMPLE D

Contact action on cotton stainers (*Dysdercus intermedius*)

Petri dishes 10 cm in diameter are lined with 1 ml of acetonic solutions of the active ingredients.

After the solvent has evaporated, 20 larvae of the penultimate stage are placed in the dishes, and the action is determined after 24 hours.

| Active ingredient from Ex. no. | Amount of active ingredient per dish (mg) | Kill rate (%) |
| --- | --- | --- |
| 1 | 0.05 | 100 |
| 2 | 0.01 | 80 |
| 3 | 0.01 | 80 |
| 4 | 0.01 | 100 |
| 5 | 0.01 | 100 |

EXAMPLE E

Contact action and effect of ingested food on caterpillars of the diamondback moth (*Plutella maculipennis*)

Leaves of young cabbage plants are dipped for 3 seconds in aqueous emulsions of the active ingredients and placed, after excess liquid has been briefly allowed to drip off, on a moist filter paper in a Petri dish. 10 caterpillars of the 4th stage of the diamondback moth are then placed on each leaf.

The action is assessed after 48 hours.

| Active ingredient from Ex. no. | Concentration of active ingredient in emulsion (wt. %) | Kill rate (%) |
| --- | --- | --- |
| 2 | 0.02 | 100 |
| | 0.01 | 80 |
| 3 | 0.02 | 100 |
| | 0.01 | 80 |
| 4 | 0.02 | 100 |
| 5 | 0.01 | 100 |
| | 0.005 | 80 |
| 6 | 0.02 | 100 |
| | 0.01 | 80 |
| 7 | 0.025 | 100 |
| | 0.01 | 80 |
| 8 | 0.02 | 100 |
| | 0.01 | 80 |
| 9 | 0.02 | 100 |
| | 0.01 | 80 |
| 10 | 0.01 | 100 |
| | 0.005 | 80 |

EXAMPLE F

Contact action on aphids (*Aphis fabae*); spray experiment

Potted bean plants (*Vicia faba*) heavily infected with aphid colonies are sprayed to runoff in a spray chamber with aqueous formulations containing various active ingredient concentrations.

The kill rate is determined after 24 hours.

| Active ingredient from Ex. no. | Concentration of active ingredient in formulation (wt. %) | Kill rate (%) |
| --- | --- | --- |
| 1 | 0.01 | 100 |
| 2 | 0.005 | 100 |
| 3 | 0.02 | 100 |
| | 0.01 | 80 |
| 4 | 0.01 | 100 |
| 5 | 0.05 | 100 |
| 6 | 0.05 | 100 |

EXAMPLE G

Contact action on ticks (*Ornithodorus moubata*)

Ticks in the 3rd larval stage are placed in paper bags and dipped for 3 seconds in the emulsion under investigation. The bags are then suspended. The action on the ticks is assessed after 48 hours.

| Active ingredient from Ex. no. | Concentration of active ingredient in emulsion (wt. %) | Kill rate (%) |
| --- | --- | --- |
| 1 | 0.04 | 100 |
| 2 | 0.04 | 100 |
| 5 | 0.04 | 100 |
| 6 | 0.04 | 100 |

We claim:

1. A pyridazinonyl-(di)(thio)-phosphoric (phosphonic) acid ester, of the formula $$\begin{array}{c} R^1 \diagdown \quad Y \\ \quad P \diagup \\ R^2X \diagup \quad \diagdown O - \text{[pyridazinone ring]} \end{array} \quad \text{I,}$$

where X and Y each denote oxygen or sulfur, $R^1$ denotes linear or branched alkyl of 1 to 4 carbon atoms, alkoxy of 1 to 4 carbon atoms, mono- or dialkylamino of 1 to 4 carbon atoms in each alkyl, phenyl, or benzyl, $R^2$ denotes linear or branched alkyl of 1 to 4 carbon atoms, phenyl or benzyl, $R^3$ denotes linear or branched alkyl of 1 to 4 carbon atoms or phenyl, $R^4$ denotes linear or branched alkyl of 1 to 4 carbon atoms, or $R^3$ and $R^4$, together with the oxygen and the carbon atom whose substituents they are, form a tetrahydropyran or tetrahydrofuran ring which may be substituted by alkyl of 1 to 4 carbon atoms.

2. The pyridazinonyl-(di)(thio)-phosphoric (phosphonic) acid ester of claim 1, wherein X denotes oxygen or sulfur, Y denotes oxygen or sulfur, $R^1$ denotes ethoxy, $R^2$ denotes ethyl or n-propyl, $R^3$ denotes linear or branched alkyl of 1 to 4 carbon atoms, and $R^4$ denotes linear or branched alkyl of 1 to 3 carbon atoms, or $R^3$ and $R^4$, together with the oxygen and the carbon atom whose substituents they are, form a tetrahydrofuran or tetrahydropyran ring.

3. The compound of the formula

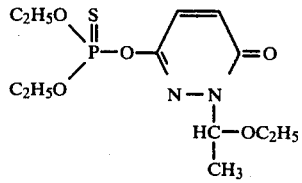

4. The compound of the formula

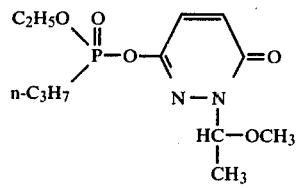

5. The compound of the formula

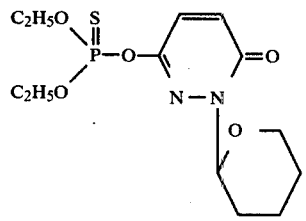

6. The compound of the formula

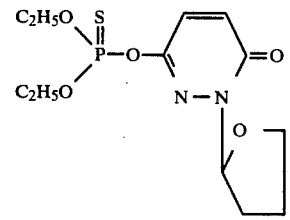

7. A pesticide comprising a solid or liquid carrier suitable for pesticide application and a pesticidally effective amount of the pyridazinonyl-(di)(thio)-phosphoric (phosphonic) acid ester of claim 1.

8. A process for combating pests, wherein the pyridazinonyl-(di)(thio)-phosphoric (phosphonic) acid ester of claim 1 is allowed to act on the pests or their habitat.

* * * * *